US006373571B1

United States Patent
Juhasz et al.

(10) Patent No.: US 6,373,571 B1
(45) Date of Patent: Apr. 16, 2002

(54) DISPOSABLE CONTACT LENS FOR USE WITH AN OPHTHALMIC LASER SYSTEM

(75) Inventors: Tibor Juhasz, Irvine, CA (US); Ronald M. Kurtz, Ann Arbor, MI (US)

(73) Assignee: IntraLase Corp., Irvine, CA (US)

( * ) Notice: Subject to any disclaimer, the term of this patent is extended or adjusted under 35 U.S.C. 154(b) by 0 days.

(21) Appl. No.: 09/266,451

(22) Filed: Mar. 11, 1999

(51) Int. Cl.[7] .......................... G01B 11/00; A61B 18/18
(52) U.S. Cl. ......................... 356/399; 356/401; 606/1; 606/5; 606/7; 606/17; 359/642; 359/708; 351/243
(58) Field of Search ................... 356/399, 401; 606/5, 13, 17, 1, 4; 359/642, 706, 708, 716; 351/230, 243

(56) References Cited

U.S. PATENT DOCUMENTS

| | | |
|---|---|---|
| 4,443,075 A | 4/1984 | Crane |
| 4,702,575 A | 10/1987 | Breglia |
| 4,712,543 A | 12/1987 | Baron |
| 4,856,513 A | 8/1989 | Muller |
| 4,905,711 A | 3/1990 | Bennett et al. |
| 5,108,412 A | 4/1992 | Xrumeich et al. |
| 5,133,708 A | 7/1992 | Smith |
| 5,171,254 A * | 12/1992 | Sher .............................. 606/166 |
| 5,336,215 A * | 8/1994 | Hsueh et al. .................... 606/4 |
| 6,254,595 B1 * | 7/2001 | Juhasz et al. .................... 606/5 |

* cited by examiner

Primary Examiner—Frank G. Font
Assistant Examiner—Layla Lauchman
(74) Attorney, Agent, or Firm—Fulbright & Jaworski, LLP

(57) ABSTRACT

A device for use in laser ophthalmic surgery includes a laser system, a disposable contact lens and an adjustable retainer ring for mounting the contact lens on the laser system. In order to properly align the disposable contact lens to the laser system, reference marks on the contact lens are brought into coincidence with predetermined focal points along the laser beam paths. To this end, the laser system successively directs a laser beam along at least three predetermined paths to respective predetermined focal points, and the contact lens is positioned across these predetermined paths. Along each predetermined path, the laser beam is activated to establish a series of laser marks on the contact lens. If the laser marks, predetermined focal points and reference marks are all coincident, then the contact lens is properly aligned with the laser system. If there is any displacement between any laser mark and reference mark, however, the retainer ring is adjusted to align all reference marks with all predetermined focal points to align the lens to the laser system.

20 Claims, 2 Drawing Sheets

DISPOSABLE CONTACT LENS FOR USE WITH AN OPHTHALMIC LASER SYSTEM

FIELD OF THE INVENTION

The present invention pertains generally to a disposable contact lens for use in laser surgery. More specifically, the present invention pertains to a contact lens that is useful for stabilizing the eye during laser ophthalmic surgery. The present invention is particularly, but not exclusively, useful as a contact lens which can be positioned against the eye to accurately align the eye with a laser source during ophthalmic laser surgery.

BACKGROUND OF THE INVENTION

It is well known that many advancements have been made in the area of ophthalmic surgery in recent years. In particular, it has happened that lasers are being more frequently used to perform certain ophthalmic surgical procedures. With presently used laser systems, however, it is a critical concern that the eye be accurately positioned in a predetermined relationship relative to the laser system. It is only when the eye can be accurately positioned relative to the laser system, that the laser beam can then be directed to the desired area inside the eye with a high degree of accuracy. This is important because an inaccurately or improperly directed laser beam could affect an unwanted area of the eye and cause permanent damage to the eye.

One way to accurately position the eye relative to a laser system, for the purposes of performing laser ophthalmic procedures, is to use a contact lens which will stabilize the eye. To do this, however, the contact lens itself must be accurately aligned with respect to the laser source. As indicated above, if the lens is not properly positioned relative to the laser source, errors in accurate positioning of the laser beam can result.

In order to ensure a correct alignment of a contact lens with a laser system, it is possible to permanently mount the lens on the laser source in a fixed orientation. If the contact lens is to remain mounted on the laser system, however, sterilization of the lens after each laser ophthalmic procedure could be time consuming, difficult to accomplish and, most likely, very uneconomical. Alternatively, the contact lens could be removed from the laser system, sterilized and replaced. Further, a disposable contact lens could be used for the laser ophthalmic procedure. For either of these last two alternatives, however, the contact lens will require realignment with the laser system after the lens is mounted on the laser system.

With the above in mind, it is an object of the present invention to provide a contact lens for laser ophthalmic surgery which can be quickly and efficiently mounted on a laser system. Another object of the present invention is to provide a contact lens which will accurately position and stabilize the eye relative to a laser system for laser ophthalmic surgery. Still another object of the present invention is to provide a method for aligning a contact lens with a laser system. Yet another object of the present invention is to provide a disposable contact lens for use in ophthalmic surgery which can be replaced with another similar contact lens. Another object of the present invention is to provide a method for mounting a contact lens on a laser system for use in ophthalmic surgery which will consistently align the lens to a predetermined orientation relative to a laser beam. Another object of the present invention is to provide an contact lens for laser ophthalmic surgery which is effectively easy to use, relatively simple to manufacture and comparatively cost effective.

SUMMARY OF THE PREFERRED EMBODIMENTS

In accordance with the present invention, a disposable contact lens for use in laser ophthalmic surgery includes a mechanism and a method for accurately aligning a laser system with the contact lens. With specific regard to the laser system of the present invention, this component generates a pulsed laser beam which has pulse durations that are chosen in a range of less than approximately three hundred picoseconds (<300 ps). Additionally, the laser beam has a wavelength that is selected from the range of approximately 0.4–1.9 micrometers (0.4–1.9 $\mu$m). In order to be effective for the purposes of the present invention, this laser system must be capable of establishing a predetermined spatial relationship with the eye of a patient.

In accordance with the present invention, the position of the laser system is based on measurements of the laser beam. Specifically, the origination point of the laser beam in the laser system is known. The laser beam can then be directed from the origination point along at least three predetermined paths. Further, the laser beam can be focused to respective predetermined focal points on each of these paths. Together, these predetermined focal points can then be used to define an alignment plane for the laser system. Once the alignment plane is identified, the contact lens then needs only to be oriented on this alignment plane in order for the contact lens to be properly positioned relative to the laser system. In order to do this, however, it is also necessary to identify a characteristic reference for the contact lens.

The contact lens of the present invention is preferably made of a clear medical grade plastic and has at least three reference marks which are placed on one of its surfaces. In the preferred embodiment of the invention, the three reference marks are placed equidistant from each other and are located near the periphery of the lens surface. Importantly, the laser system based reference (i.e. the predetermined focal points) and the contact lens based reference (i.e. the reference marks on the contact lens surface) must be compatible. Therefore, the reference marks are placed on the lens so that they will be coincident with the predetermined focal points of the laser beam when the contact lens is properly aligned with the laser system.

To engage the disposable contact lens with the laser system, the contact lens is mounted on a retainer ring that is affixed to the system. More specifically, there are three adjusters that interconnect this retainer ring with the laser system which, in concert, can be operated to adjust the position of the retainer ring relative, and hence the contact lens, to the laser system. Importantly, the retainer ring also positions the contact lens to intersect the predetermined paths of the laser beam.

With the contact lens mounted on the retainer ring, the laser beam is focused to a focal point on the surface of the contact lens. Once so focused, the laser beam is activated to etch a laser mark onto the surface. This process is repeated for each of the three predetermined paths to establish three laser marks on the surface of the contact lens. Recall, the reference marks on the contact lens are respectively coincident with the predetermined focal points of the laser beam when the contact lens is properly aligned with the laser system. It then follows that if the laser marks are coincident with the reference marks, the contact lens is in proper alignment. On the other hand, it there is any displacement $\Delta$ between a reference mark and its respective laser mark, then the contact lens is somehow tilted relative to the laser system. Stated differently, the lens plane and the alignment plane are not coplanar. To align the lens to the laser system for laser ophthalmic surgery, the lens must then be moved to make all reference marks on the contact lens coincident with their respective predetermined focal points.

As implied above, the length of the adjusters can be modified automatically by a control system to tilt the contact lens into alignment with the laser system. To do this, the control system will receive an input signal that is indicative of a displacement Δ, between each reference mark and its respective laser mark. This input signal, which represents the measurable displacement Δ values, is then compared with known geometric relationships which are preprogrammed into the control system to generate an error signal. The control system then appropriately changes the lengths of the adjusters to tilt the retainer ring into an alignment position, and thereby minimize the error signal.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENT

Figure 1:
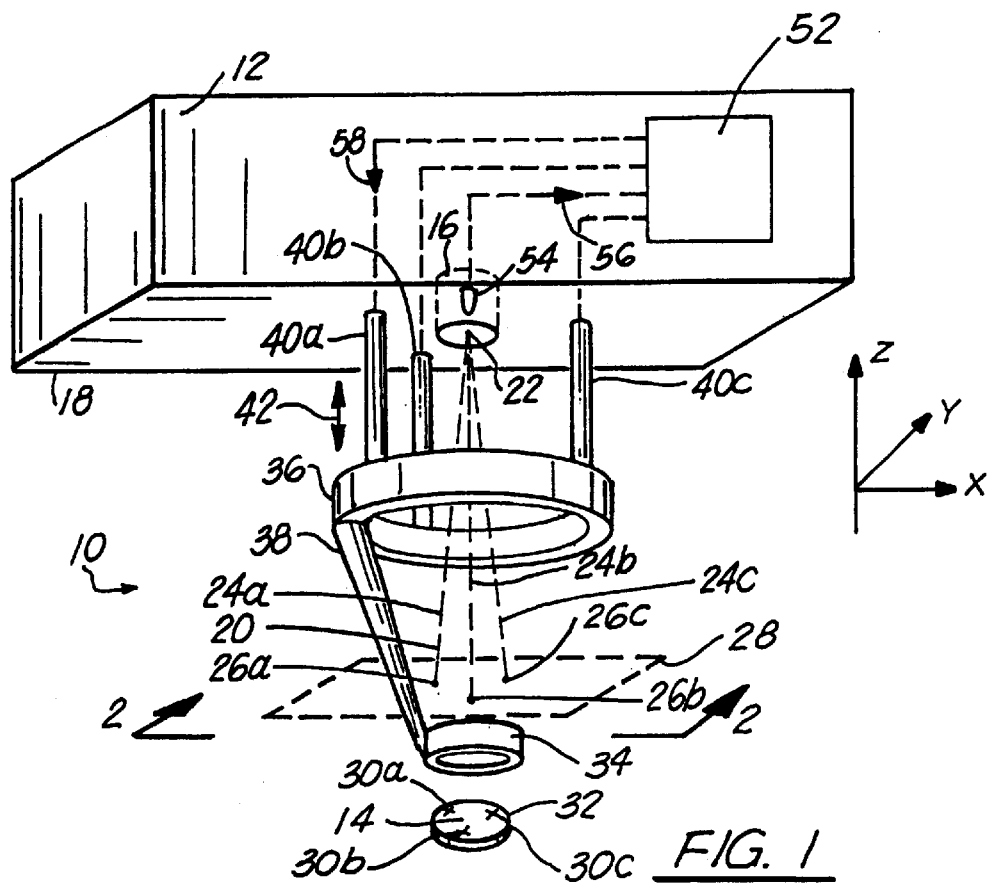
FIG. 1 is a perspective view of the laser system and the contact lens of the present invention.

Referring initially to FIG. 1, the contact lens and device for laser ophthalmic surgery in accordance with the present invention is shown and generally designated 10. As shown in FIG. 1, the major components of the device 10 are a laser system 12 and a contact lens 14. To accomplish the laser ophthalmic surgery, the laser system 12 includes a laser source 16 which is mounted on the system housing 18. This laser source 16 generates a laser beam 20 from an origination point 22, as shown in FIG. 1. In the preferred embodiment of the invention, the laser beam 20 has a pulse duration less than three hundred picoseconds (<300 ps) and a wavelength of between approximately 0.4–1.9 micrometers (0.4–1.9 μm).

FIG. 1 shows that the laser beam 20 can be directed along at least three predetermined paths 24, of which the paths 24a, 24b and 24c are representative. Further, there is a predetermined focal point 26 along each predetermined path 24 of which the focal points 26a, 26b and 26c are representative. In the preferred embodiment of the invention, the focal points 26 are equidistant from the origination point 22, and together these focal points 26 define an alignment plane 28. This alignment plane 28 represents the desired planar orientation for the lens 14 relative to the system 12.

For the purpose of correctly aligning the contact lens 14 to the laser system 12, at least three prepositioned reference marks 30, of which the marks 30a, 30b and 30c are representative, are placed on the contact lens 14 during manufacture. In the preferred embodiment of the invention, three reference marks 30 are placed equidistant from each other near the periphery 32 of the contact lens 14 substantially as shown in FIG. 1. Importantly, the reference marks 30 are placed on the lens 14 so that the reference marks 30 will be coincident with their respective predetermined focal points 26 on the laser beam 20 when the contact lens 14 is properly aligned with the laser system 12.

Before the contact lens 14 can be properly aligned with the laser beam 20, the lens 14 must be attached to the laser system 12 and positioned to intersect the predetermined paths 24. To do this, the contact lens 14 is selectively mounted on a retainer ring 34. Further, the retainer ring 34 is oriented relative to the laser system 12 so that once the contact lens 14 is mounted on the retainer ring 34, the lens 14 is also positioned across all predetermined paths 24. With this orientation, the retainer ring 34 is fixedly connected to an attachment ring 36 with an extension arm 38. As shown in FIG. 1, at least three telescopic adjusters 40, of which the adjusters 40a, 40b and 40c are representative, connect the attachment ring 36 with the housing 18 of laser system 12. Each adjuster 40 can be extended or shortened in the direction as shown by arrow 42 to vary the distance and the orientation of the attachment ring 36 relative to the housing 18. Thus, the adjusters 40 are either extended or shortened, and the attachment ring 36 can be made to tilt about the x-axis or the y-axis. It follows that as the attachment ring 36 tilts, the retainer ring 34 also tilts. Once the contact lens 14 is attached to the retainer ring 34, it will also move and tilt along with the retainer ring 34. In this manner, the position of the contact lens 14 can be adjusted for purposes of aligning the contact lens 14 with the laser system 12.

Figure 2A:
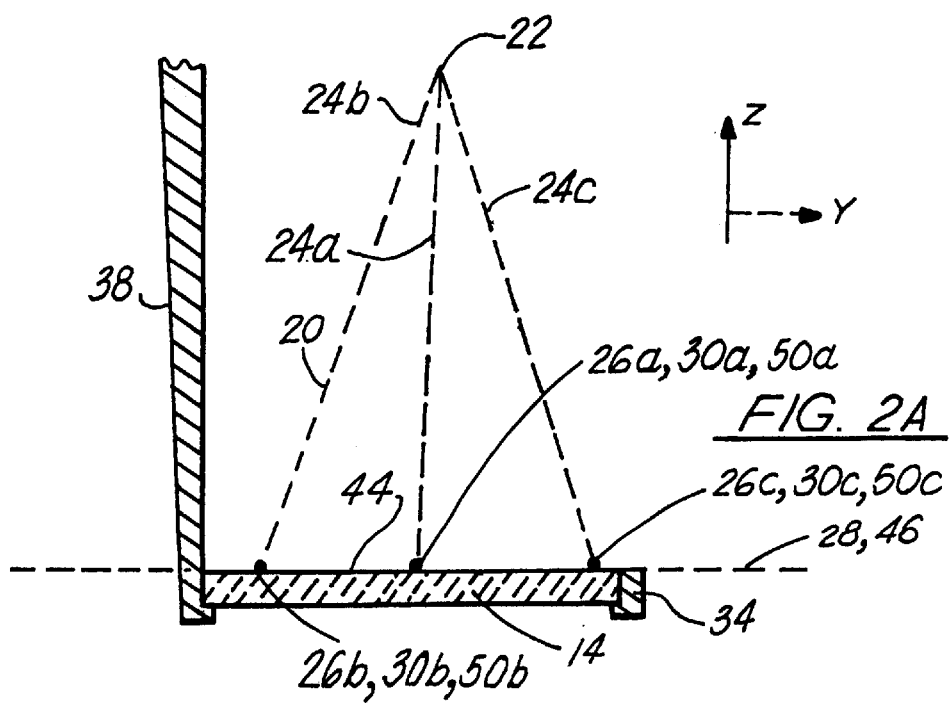
FIG. 2A is a cross-sectional view of the contact lens showing a relationship between the lens plane established by reference marks on the lens and the alignment plane established by the laser system when the contact lens is properly aligned with the laser system, as seen along line 2—2 in FIG. 1.

The manner in which the laser beam 20 of laser system 12 interacts with the reference marks 30 on contact lens 14 to align the lens 14 with the system 12 is best appreciated by referring to FIG. 2A. By referring to FIG. 2A it will be appreciated that the three reference marks 30a–c on the surface 44 of contact lens 14 will together define a lens plane 46. Further, as disclosed above, the three predetermined focal points 26a–c together will also define an alignment plane 28. The object then in aligning the contact lens 14 with laser system 12 is to bring the lens plane 46 into alignment (coplanar) with the alignment plane 28. To make this adjustment, it is necessary to somehow determine how far off the planes 28 and 46 are from being coplanar. For the present invention, this is accomplished by determining the actual relationship of the lens plane 46 relative to the laser system 12 and then comparing the actual relationship to the desired relationship.

As shown in FIG. 2A, in order to determine its actual relationship with the laser system 12, the contact lens 14 is positioned across at least three predetermined paths 24 of the laser beam 20. With the contact lens 14 in this position, the laser beam 20 is sequentially directed along each path 24 and respectively focused onto the surface 44 of lens 14. For each path 24, the laser beam 20 is then activated in sequence to etch a respective laser mark 50 on the contact lens 14. For example, the laser mark 50b is the result of directing the laser beam 20 along the path 24b. All of the laser marks 50a–c will be in the lens plane 46.

Recall that the reference marks 30a–c define lens plane 46. Specifically, they are placed and oriented on the contact lens 14 so that they will coincide with the predetermined focal points 26 of the laser beam when the contact lens 14 is properly aligned with the laser system 12. Thus, if the laser marks 50a–c are coincident with the reference marks 30a–c, they will also be coincident with the predetermined focal points 26. This condition is shown in FIG. 2A and means the lens plane 46 and alignment plane 28 are substantially coplanar. Thus, the lens 14 is properly aligned with the laser system 12. On the other hand, if there is a displacement Δ between any reference mark 30 and its respective laser mark 50, then the lens 14 is somehow tilted.

Figure 2B:
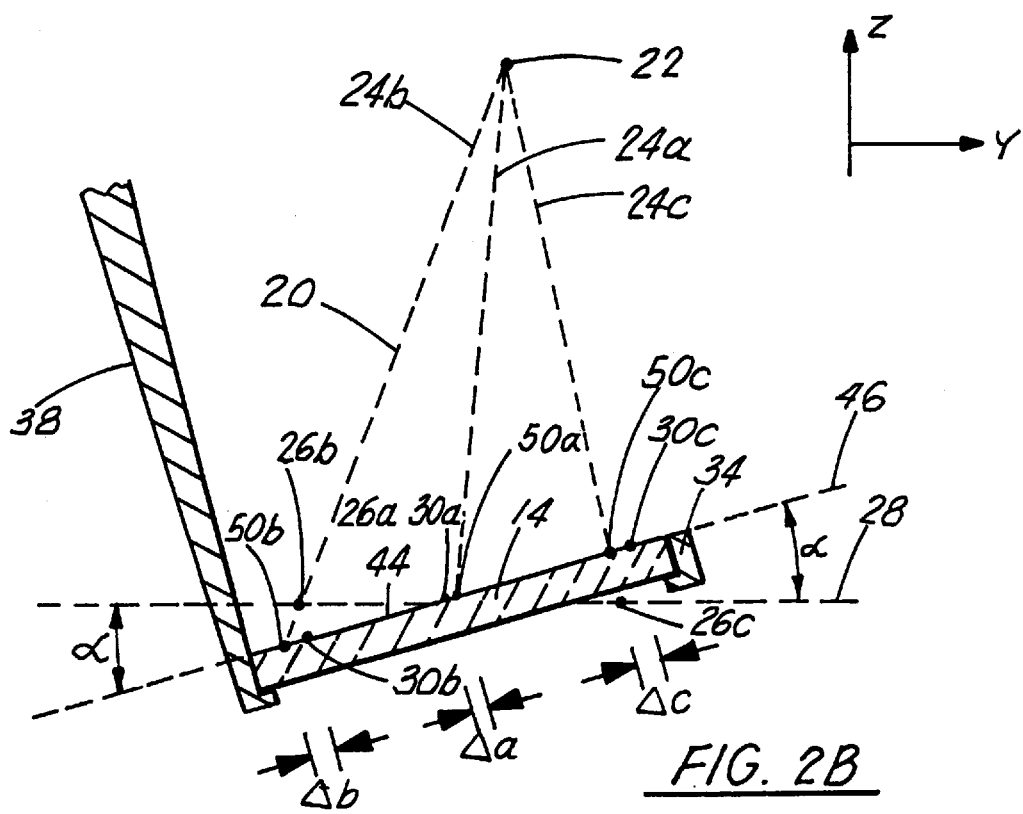
FIG. 2B is a cross-sectional view of the contact lens showing a relationship between the lens plane established by reference marks on the lens and the alignment plane established by the laser system when the contact lens is properly aligned with the laser system, as seen along line 2—2 in FIG. 1.

FIG. 2B illustrates a situation where the contact lens 14 is substantially tilted about the x-axis. As shown in FIG. 2B, reference mark 30b is displaced from laser mark 50b by a distance Δb, and the lens plane 46 intersects the alignment plane 28 and creates an angle α. Using well known geometric relationships, the adjusters 40 can be manipulated to establish α=0 and to make the reference marks 30 coincident with the predetermined focal points 26. Similar geometric computations can be made to correct a tilting of the lens 14 about the y-axis, or for simultaneous tilt of the lens 14 about both the x-axis and the y-axis.

To determine how much extension or shortening is required of each adjuster 40, and referring back to FIG. 1, a control system 52 is included within the laser system 12. This control system 52 is in signal communication both with the adjusters 40 and with an optical system 54 included within the laser source 16. The optical system 54 measures the displacement Δ discussed above, if any, between each respective laser mark 50 and reference mark 30. Based on these measurements, the optical system 54 sends a series of input signals which are indicative of the displacements Δ to the control system 52, as shown by arrow 56. Once received at the control system 52, each signal is then compared with known geometric relationships between the laser marks 50, reference marks 30 and predetermined focal points 26 which are preprogrammed into the control system 52.

Based on the comparison between the respective laser marks 50, laser marks 30 and predetermined focal points 26, the control system 52 generates an error signal. The control system 52 then sends a signal to each adjuster 40, of which a representative signal is shown by arrow 58. Each adjuster 40, in response to the signal from the control system 52, lengthens or shortens as required to tilt the lens 14 about the x-axis and the y-axis. After the lens 14 is tilted in response to the control system 52, a new set of laser marks 50 can be established. As the lens 14 becomes aligned with the laser system, the displacement Δ between each reference mark 30 and its respective laser mark 50 is minimized, which minimizes the error signal generated by the control system 52. In this manner, the control system 52 automatically positions the lens 14 in order to align the lens 14 with the laser beam 20.

Figure 3:
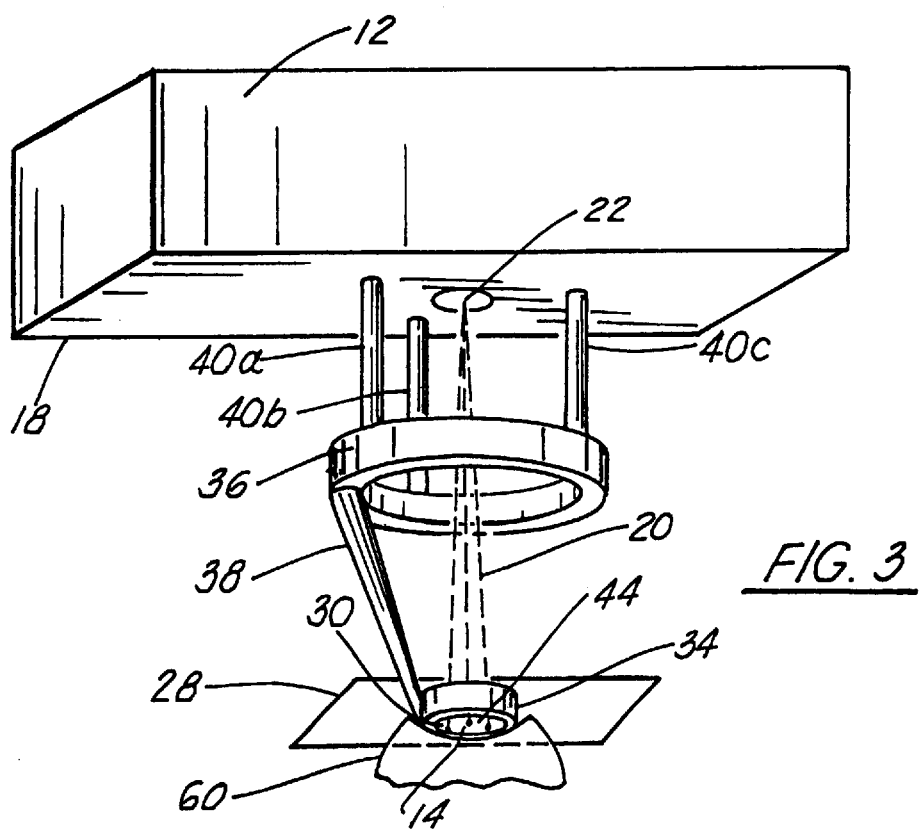
FIG. 3 is a perspective view of an eye stabilized by the contact lens with the contact lens aligned on the laser system.

FIG. 3 shows the aligned contact lens 14 and device 10 of the present invention. After alignment, the lens surface 46 is coplanar with the alignment plane 28, and the reference marks 30 are substantially aligned with the predetermined focal points 26. Once the lens 14 is aligned with the laser beam 20, the human eye 60 is accurately centered on the lens 14 and stabilized in preparation for laser ophthalmic surgery. Because the lens 14 will be in contact with the human eye 60 during the laser ophthalmic procedure, the disposable contact lens 14 is preferably made of a medical grade plastic for sterilization purposes. After the laser surgery, the disposable contact lens 14 is discarded.

While the particular disposable contact lens for use with an ophthalmic laser system as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A device for use in ophthalmic surgery, which comprises:
    a laser system for generating a laser beam from an origination point, along at least three predetermined paths to at least three respective predetermined focal points;
    a contact lens having a first surface and a second surface and a periphery, said contact lens having at least three reference marks placed on said first surface of said contact lens, said contact lens being positioned across said predetermined paths; and
    a means for adjusting said contact lens to coincide said plurality of predetermined focal points with said plurality of reference marks.

2. A device as recited in claim 1, wherein said means for adjusting said contact lens further comprises:
    a retainer ring;
    at least three adjusters interconnecting said retainer ring with said laser system, each said adjuster being individually activated to move said retainer ring relative to said laser system; and
    a means for temporarily mounting said contact lens on said retainer ring for movement therewith.

3. A device as recited in claim 2 wherein said adjusters are substantially equidistant from each other.

4. A device as recited in claim 1 wherein said reference marks are substantially equidistant from each other.

5. A device as recited in claim 1 wherein said contact lens is made of a medical grade plastic.

6. A device as recited in claim 1 wherein said laser beam has a wavelength and a pulse duration and said wavelength is selected from a range of approximately 0.4–1.9 μm ($0.4 < \lambda < 1.9$ μm) and said pulse duration is less than three hundred picoseconds (<300 ps).

7. A device as recited in claim 1 wherein said predetermined focal points are substantially equidistant from said origination point.

8. A device as recited in claim 1 wherein said reference marks are placed near said periphery of said first surface of said contact lens.

9. A device as recited in claim 1 wherein said contact lens is moved from a first position wherein at least one said reference mark has a displacement Δ from said respective focal point to a second position wherein all said reference marks are coincident with said respective focal points.

10. A device as recited in claim 9 further comprising:
    means for determining said distance Δ; and
    a control system in signal communication with said adjusting means to minimize said distance Δ.

11. A device as recited in claim 1 wherein said laser system is activated to establish at least three laser marks on said first surface of said contact lens for alignment of said reference marks with said predetermined focal points.

12. A device for use in ophthalmic surgery, which comprises:
    a laser system for generating a laser beam from an origination point, said laser beam being directed along at least three predetermined paths to at least three respective predetermined focal points, said focal points defining a alignment plane;

a contact lens having a first surface and a second surface and a periphery, said contact lens having at least three reference marks placed on said first surface to define a lens plane; and a means for adjusting said contact lens to a position wherein said alignment plane is substantially coplanar with said lens plane.

13. A device as recited in claim 12, wherein said means for adjusting said contact lens further comprises:

a retainer ring;

at least three adjusters interconnecting said retainer ring with said laser system, each said adjuster being individually activated to move said retainer ring relative to said laser system; and a means for mounting said contact lens on said retainer ring for movement therewith.

14. A device as recited in claim 13 wherein said adjusters are substantially equidistant from each other.

15. A device as recited in claim 13 wherein said reference marks are substantially equidistant from each other.

16. A device as recited in claim 12 wherein said contact lens is made of a medical grade plastic.

17. A device as recited in claim 12 wherein said laser beam has a wavelength and a pulse duration and said wavelength is selected from a range of approximately 0.4–1.9 $\mu$pm (0.4<$\lambda$<1.9 $\mu$m) and said pulse duration is less than three hundred picoseconds (<300 ps).

18. A device as recited in claim 11 wherein said contact lens is moved from an unaligned position, wherein said alignment plane intersects said lens plane to form an angle $\alpha$, to an aligned position wherein said alignment plane is substantially coplanar with said lens plane.

19. A device as recited in claim 12 wherein said reference marks are placed near said periphery of said first surface of said contact lens.

20. A method for positioning a contact lens for laser ophthalmic surgery, comprising the steps of:

providing a laser system for generating a laser beam from an origination point;

sequentially directing said laser beam along at least three predetermined paths to at least three respective predetermined focal points;

placing a contact lens in a retainer ring to position said contact lens across said predetermined paths, said contact lens having a first surface and a second surface, said contact lens having at least three reference marks on said first surface;

interconnecting said retainer ring and said laser system with at least three adjusters, each said adjuster being individually activated to move said retainer ring relative to said laser system;

successively activating said laser beam along each said predetermined path to create a respective laser mark on said contact lens;

measuring a displacement $\Delta$ between each said laser mark and said respective reference mark; and manipulating said adjusters to adjust the position of said contact lens to minimize said displacement $\Delta$ in order to align said predetermined focal points with said reference marks.

\* \* \* \* \*